United States Patent [19]

Goldberg et al.

[11] Patent Number: 4,762,782

[45] Date of Patent: Aug. 9, 1988

[54] ASSAY FOR BETA-LACTAM ANTIBIOTICS

[75] Inventors: Edward B. Goldberg, Brookline; James T. Park, Weston, both of Mass.

[73] Assignee: Micromol Corporation, Boston, Mass.

[21] Appl. No.: 734,535

[22] Filed: May 16, 1985

[51] Int. Cl.[4] .............. G01N 33/535; G01N 33/543; G01N 33/566; G01N 33/577
[52] U.S. Cl. ........................................ 435/7; 435/188; 435/810; 435/820; 436/501; 436/503; 436/518; 436/548; 436/808; 436/815; 436/822; 530/391; 530/807
[58] Field of Search .................. 435/172.2, 240, 948, 435/7, 810, 820, 188; 436/501, 503, 518, 815, 822, 548; 530/389, 808, 809, 391, 807

[56] References Cited

U.S. PATENT DOCUMENTS 4,596,768  6/1986  Singh et al. ..................... 435/7

OTHER PUBLICATIONS

G. Kleppe et al, *Journ. Biol. Chem.*, 254, 4856–4862, 1979.

Primary Examiner—Sidney Marantz
Assistant Examiner—David A. Saunders
Attorney, Agent, or Firm—Andrew F. Kehoe

[57] ABSTRACT

An improved assay for measuring the quantity of Beta-lactam antibiotics, particularly valuable for measuring penicillin in milk. The assay includes the covalent-attachment of a penicillin to a penicillin-binding-protein bound to a matrix, the highly selective attachment of an antibody to such a conjugate, and the detection and measurement of the quantity of resulting antibody-complex material as a direct measure of the amount of penicillin in the milk being tested.

17 Claims, No Drawings

ASSAY FOR BETA-LACTAM ANTIBIOTICS

BACKGROUND OF THE INVENTION

Government regulations forbid the use of milk containing more than 0.01 units of penicillin per ml in products intended for human consumption. This poses a problem for dairy producers who use large doses of Beta-lactam-type antibiotics such as penicillin to control mastitis or other diseases in dairy cows and must monitor milk for excessive quantities of these antibiotics such as penicillins or cephalosporins. An improved rapid, accurate, and easy-to-use assay procedure that can measure low concentrations of such antibiotics, particularly penicillin, in milk would be of value to the dairy industry.

A number of tests for detecting and measuring antibiotics in milk are known in the literature. U.S. Pat. No. 4,239,852 discloses a penicillin-detection test utilizing microbiological cell parts having good affinity for penicillin. The cell parts have penicillin receptor sites and the penicillin in milk competes with an added known quantity of tagged penicillin for binding to these sites. The greater the quantity of penicillin in the milk, the smaller the quantity of tagged penicillin will be accepted by the receptor sites. Thus, in a typical test, the amount of penicillin is measured as an inverse function of the amount of tagged penicillin that becomes attached to the cell parts. U.S. Pat. No. 4,239,745 discloses a somewhat similar test procedure wherein a penicillin-attracting microorganism itself, rather than a cell part thereof, is utilized.

Still another process for testing for penicillin in milk is disclosed in U.S. Pat. No. 4,347,312 wherein Brown et al disclose the use of antibody bound to a matrix as a means of anchoring penicillin selectively.

The above tests are not altogether satisfactory, because they fail to provide a simple means to measure an indicator tag directly (as opposed to inversely) proportional to the penicillin being detected, or because they are too cumbersome and expensive. These in direct competition assays are inherently less sensitive than direct tests, because the background levels with no penicillin in the milk are high and it takes a relatively greater amount of competing penicillin to reduce the level sufficiently to obtain a significant and reproducible result.

The Inventors have directed their efforts to develop a new assay which will be advantageous to the dairy operator, to the milk trucker, and to the individual farmer.

SUMMARY OF THE INVENTION

It is a principal object of the invention to provide an improved Beta-lactam antibiotic assay test.

Another object of the invention is to provide a more dependable assay test, one that can be readily used with indicators such that the tester measures the quantity of indicator material as a direct measure of the amount of penicillin in the sample being tested.

Another object of the invention is to provide a faster and more highly dependable assay test.

Other objects of the invention include the provision of a general process for carrying out the test of the invention.

Another object of the invention is to provide a test kit utilizing the process of the invention.

Still another object of the invention is to provide specific reactants which are useful in carrying out the test of the invention. Such reactants include (a) a penicillin-bearing conjugate (sometimes called P-PBP, herein) against which a highly-specific antibody can be prepared, (b) the reaction product of such a highly-specific antibody with said conjugate and (c) the reaction product defined as (b) with an enzyme incorporated therein.

Other objects of the invention will be obvious to those skilled in the art on their reading of this disclosure.

The process of the invention uses a highly sensitive penicillin-binding protein, attached to a matrix, to react covalently with the penicillin present liquids, particularly aqueous liquids such as in a milk sample and thereby to form a complex molecule of penicillin and the penicillin-binding protein. An avid antibody, highly specific for the attached penicilloyl group, is used to bind strongly to the penicilloyl-penicillin-binding-protein which has formed on the matrix. The antibody can have covalently attached to it, a suitable tag (e.g. one of a number of a commercially-available materials such as horse radish peroxidase, glucoamylase, alkaline phosphatase, glucose oxidase, and Beta-D-galactosidase. Such tags are used to help to quantitate the amount of antibody bound to the penicilloyl groups. After milk-borne penicillin and antibody-enzyme conjugate have been allowed to bind to the matrix-anchored penicillin-binding protein for a suitable time, the matrix is washed. Thus any unbound penicillin or any residual unbound antibody-enzyme conjugate and any milk is washed away. What remains on the matrix is the penicillin-binding protein/penicilloyl/antibody/enzyme material. A number of detection means are available for use in identifying and quantifying this material. One appropriate detection means is a chromogenic-substrate. The chromogenic substrate is combined with the penicillin-binding protein-penicilloyl-antibody-enzyme material and the amount of color produced from this chromogenic-bearing substrate by the enzyme bound to the matrix is determined. The amount of color developed and measured will be directly proportional to the amount of penicillin present in the milk.

The selection of many appropriate enzymes, substrates, and matrices can be made readily from those commercially-available materials already used in the art by anyone skilled in the immunoassay art, upon their reading of the disclosure. The conjugation of such tags, including such an enzyme, to an antibody as described herein is also a standard manipulative procedure for one skilled in immunoassay techniques. See for example, O'Sullivan, M. J. and Marks V. (1981) Methods for the Preparation of Enzyme-Antibody Conjugates for use in Enzyme Immunoassay, in Methods in Enzymology (ed J. J. Langone & H. Van Vunakis), Academic Press, New York, Vol. 73, pp 147–166. Some special components required for the present method are a (1) a suitable penicillin-binding protein and (2) a penicilloyl specific antibody. Applicant's describe herein how plentiful and economic supplies of these materials can be obtained.

The penicillin-binding protein (PBP) must be highly sensitive to penicillin (e.g. PBP-1a, PBP-1b, PBP-2a or PBP-4 from *Bacillus subtilis;* reference: Kleppe, G. and Strominger, J. L. 1979. J. Biological Chemistry 254: 4856–4862 or any similar PBP). These PBPs can be produced in quantity by cloning the appropriate gene in a vector with a strong, inducible promotor to make a high production vector. Those skilled in the art of genetic engineering can choose one of several vectors derived from pBR322 or phage lambda (e.g. pPL-lambda available from Pharmacia-PL Biochemicals) for cloning. Multiple copies of the gene can then be produced and expressed in *Escherichia coli*, or another appropriate bacterial host, to make a high production strain of the bacteria, all according to techniques known to those skilled in the art.

The penicilloyl specific antibody (or the penicilloyl-peptide specific antibody) can be obtained in an economically-feasible manner from a monoclonal-antibody-producing cell. The antibody should react avidly with the penicilloyl-penicillin-binding-protein complex formed during incubation of the milk sample with the penicillin-binding protein. However, it must not react to any significant extent with the penicillin-binding-protein alone or the penicillin alone. The procedure of selecting, after hybridization, such monoclonal antibody producing immortalized cells from, e.g. a population of mouse spleen cells from a mouse which has been immunized with penicilloyl-penicillin-binding-protein (P-PBP) is straightforward for one practiced in the art of growing and selecting specific monoclonal antibodies. See for example, Glafre, G. and Milstein, C. (1981) Preparation of Monoclonal Antibodies: Strategies and Procedures in Methods in Enzymology (ed J. J. Langone and H. Van Vunakis), Academic Press, New York, Vol. 73, pp 3–46.

Another acceptable procedure for preparing the antibody includes injecting an animal with the P-PBP, absorbing the immune serum against penicillin-binding protein, and using the supernatant, or eluate, i.e. the fraction of the fluid bearing the P-PBP-selective antibody.

It is also possible to utilize a penicillin-antigen such as penicillin-bovine serum albumin (P-BSA) instead of P-PBP in these procedures.

ILLUSTRATIVE EXAMPLES OF THE INVENTION

In this application there is described a preferred embodiment of the invention and suggested various alternatives and modifications thereof, but it is to be understood that these are not intended to be exhaustive and that other changes and modifications can be made within the scope of the invention. These suggestions herein are selected and included for the purposes of illustration in order that others skilled in the art will more fully understand the invention and the principles thereof and will be able to modify it and embody it in a variety of forms, each as may be best suited to the condition of a particular case.

The following is a list of components conveniently utilized in test kits for carrying out the assay of the invention:

1. Penicillin-G (for use in positive calibration or check of test, if desired)
2. Penicillin-Binding-Protein from a high-production bacterial cell strain for the penicillin-binding-protein as described above.
3. Matrix-penicillin-binding-protein. (The matrix is conveniently an appropriate plastic or glass tube or stick to which the penicillin-binding protein has been attached in the standard manner).
4. Antibody(monoclonal)
5. Enzyme label from commercial sources (examples: horseradish peroxidase, Beta-galactosidase, alkaline phosphatase). Radioactive, fluorescent, and other tagging systems known to the art can be used when particular circumstances make them desirable.
6. Chromogenic substrate to complement the specific enzyme lable selected for use.
7. A tagged antibody such as an enzyme-antibody conjugate, formed according to standard methods in the art, such as a conjugate of (5) and (6) of this list.
8. Color Standards or instrument such as a simple color comparator to quantitatively read the tag.

A typical procedure relates to the testing for penicillin-G in milk:

The gene for PBP-2a, a penicillin-binding-protein (PBP) prepared from *Bacillus subtilis*, is cloned in the vector pPL lambda. This PBP is supplied in a test kit in the form of lyophilized protein absorbed to the bottom of a test tube which serves as a matrix. A quantity of about 1 ml of milk is added to the test tube. Also added is a penicilloyl-specific antibody (prepared from a population of mouse-spleen cells from a population of mice immunized with a PBP-penicillin complex). This antibody is tagged with the enzyme Beta-galactosidase and may be designated as (E-Ab). The mixture is best incubated at 37° C. for 5 minutes. During this time the penicillin binds to the PBP and the antibody-enzyme conjugate binds to the penicilloyl-PBP that is fixed to the matrix.

The product is washed free of excess reactants by rinsing with neutral buffered physiological saline. The test tube (substrate) now has attached to it an amount of antibody-enzyme conjugate that is proportional to the amount of penicillin G in the milk sample. The amount of Beta-galactosidase present (which reflects directly the amount of penicillin in the milk) is determined by addition of 1 ml of 0.001M ortho nitrophenyl Beta-galactoside (the chromogenic substrate) followed by incubation at 37° C. for 5 minutes. Alternatively, incubation may be carried out at room temperature for the required period for the color to develop. Samples of milk completely lacking penicillin and samples containing exactly 0.01, 0.03 and 0.1 units of penicillin per ml serve as controls against which the unknown samples are compared. The color is directly proportional to the amount of penicillin in the milk being tested.

EXAMPLE 2

Another example of such a test procedure is the measurement of a different Beta-lactam antibiotic, i.e. the cephalosporin, called cephalexin. The above example is repeated except that a highly sensitive cephalexin-binding protein is used to bind the cephalexin and an antibody, specific to the resulting cephalexoyl/cephalexin-binding protein, is used. A good quantitive test of the antibiotic in milk is obtained.

It is also to be understood that the following claims are intended to cover all of the generic and specific features of the invention herein described and all statements of the scope of the invention which might be said to fall therebetween.

What is claimed is:

1. A test method for assaying a Beta-lactam antibiotic in an aqueous liquid medium, said process comprising the steps of
   (a) contacting said liquid to be tested with an antibiotic-binding-protein attached to a matrix and specific for said antibiotic to form a conjugate between (A) said antibiotic in said liquid and (B) said antibiotic-binding protein;

(b) contacting said conjugate with an antibody that specifically binds to said conjugate of (A) and (B) but does not specifically bind to either (A) or (B) in non-conjugated form;

(c) quantitatively analyzing the amount of product formed by binding between said conjugate and said antibody as a measure of said antibiotic in said liquid.

2. A test method as defined in claim 1 wherein said Beta-lactam antibiotic is a cephalosporin.

3. A test method as defined in claim 2 wherein said cephalosporin is cephalexin.

4. A test methods as defined in claim 1 wherein an enzyme tag is chemically bonded to said antibody.

5. A test method as defined in claim 4 wherein said liquid is milk.

6. A method as defined in claim 1 wherein said antibiotic is penicillin.

7. A test defined in claim 6 wherein said penicillin is Penicillin G.

8. A test method as defined in claim 6 wherein said penicillin-binding-protein is selected from the group of consisting of PBP-1a, PBP-1b, PBP-2a, or PBP-4 of *Bacillus subtilis*.

9. A test method as defined in claim 6 wherein said liquid is milk.

10. A test method as defined in claim 9 wherein an enzyme indicator-activity tag is chemically bonded to said antibody.

11. A test method as defined in claim 6 wherein said antibody is a monoclonal antibody raised against penicilloyl-antigen.

12. A test as defined in claim 11 wherein said penicilloyl antigen is a conjugate of penicillin and bovine serum albumin.

13. A test method as defined in claim 11 wherein said penicilloyl-antigen is said conjugate of penicillin and penicillin-binding-protein.

14. A test method as defined in claim 13 wherein said liquid is milk.

15. A kit useful in the assaying of Beta-lactam antibiotic in milk, said kit comprising (a) a matrix carrying an antibiotic-binding protein for said Beta-lactam antibiotic;

(b) an antibody reactant specific for the reaction product of said Beta-lactam antibiotic-binding protein with said antibiotic said antibody reactant having an indicator-enhancing tag covalently bonded to said antibody reactant; and (c) an indicator forming means to provide a visual indication of the presence of said antibody complexed with said antibiotic-binding protein and said Beta-lactam antibiotic.

16. A kit as defined in claim 15 wherein said indicator enhancing tag is an enzyme.

17. An antibody reactant which is specific for the reaction product of a Beta-lactam-antibiotic-binding protein with said Beta-lactam antibiotic, said antibody reactant having covalently bonded thereto, an indicator-enhancing tag.

* * * * *